United States Patent [19]

Thoer et al.

[11] Patent Number: 4,755,613

[45] Date of Patent: Jul. 5, 1988

[54] FORMYLATION PROCESS FOR PRODUCING ALDEHYDES

[75] Inventors: Annick Thoer, St Germain Les Arpajon; Ghislain Denis, Toulouse; Michel Delmas, Auzeville Tolosane; Antoine Gaset, Toulouse, all of France

[73] Assignee: Institut National Polytechnique, Toulouse, France

[21] Appl. No.: 37,259

[22] PCT Filed: Jun. 20, 1986

[86] PCT No.: PCT/FR86/00216

§ 371 Date: Apr. 10, 1987

§ 102(e) Date: Apr. 10, 1987

[87] PCT Pub. No.: WO87/00167

PCT Pub. Date: Jan. 15, 1987

[30] Foreign Application Priority Data

Jul. 10, 1985 [FR] France ............................ 85 10907

[51] Int. Cl.$^4$ ........................................... C07C 301/19
[52] U.S. Cl. ................................. 549/530; 568/347
[58] Field of Search ..................... 568/347; 549/530

[56] References Cited

U.S. PATENT DOCUMENTS 3,206,513  9/1965  Budde ................................ 568/347
3,365,500  1/1968  Ponty ................................. 568/347
3,972,945  3/1976  Albright ............................. 568/347
4,584,410  4/1986  Hamada et al. ..................... 568/347

FOREIGN PATENT DOCUMENTS 0068725  1/1983  European Pat. Off. ............ 568/437
48-3829   2/1973  Japan ................................. 568/437

OTHER PUBLICATIONS

Smith et al., J. Org. Chem., vol. 50, pp. 790–792 (1985).
Deshpande, Chem. Abst.; vol. 66, #55265H (1967).
Hine et al., J.A.C.S., vol. 81, pp. 6446–6449 (1959).

*Primary Examiner*—James H. Reamer
*Attorney, Agent, or Firm*—Harold H. Dutton, Jr.

[57] ABSTRACT

The invention relates to a process for preparing aromatic or hetero-aromatic aldehydes by the Reimer-Tiemann formylation reaction. The process comprises employing a solid alkaline hydroxide in order to carry out the reaction in a solid/liquid medium and by adjusting the initial hydration rate of the medium to be higher than 0.05 moles of water per mole of initial compound and less than 1.5 moles of water per mole of alkaline hydroxide initially in the medium. Such a process makes it possible to substantially increase the yield of the Reimer-Tiemann reaction and to avoid tar formation entirely or in large part.

12 Claims, 1 Drawing Sheet

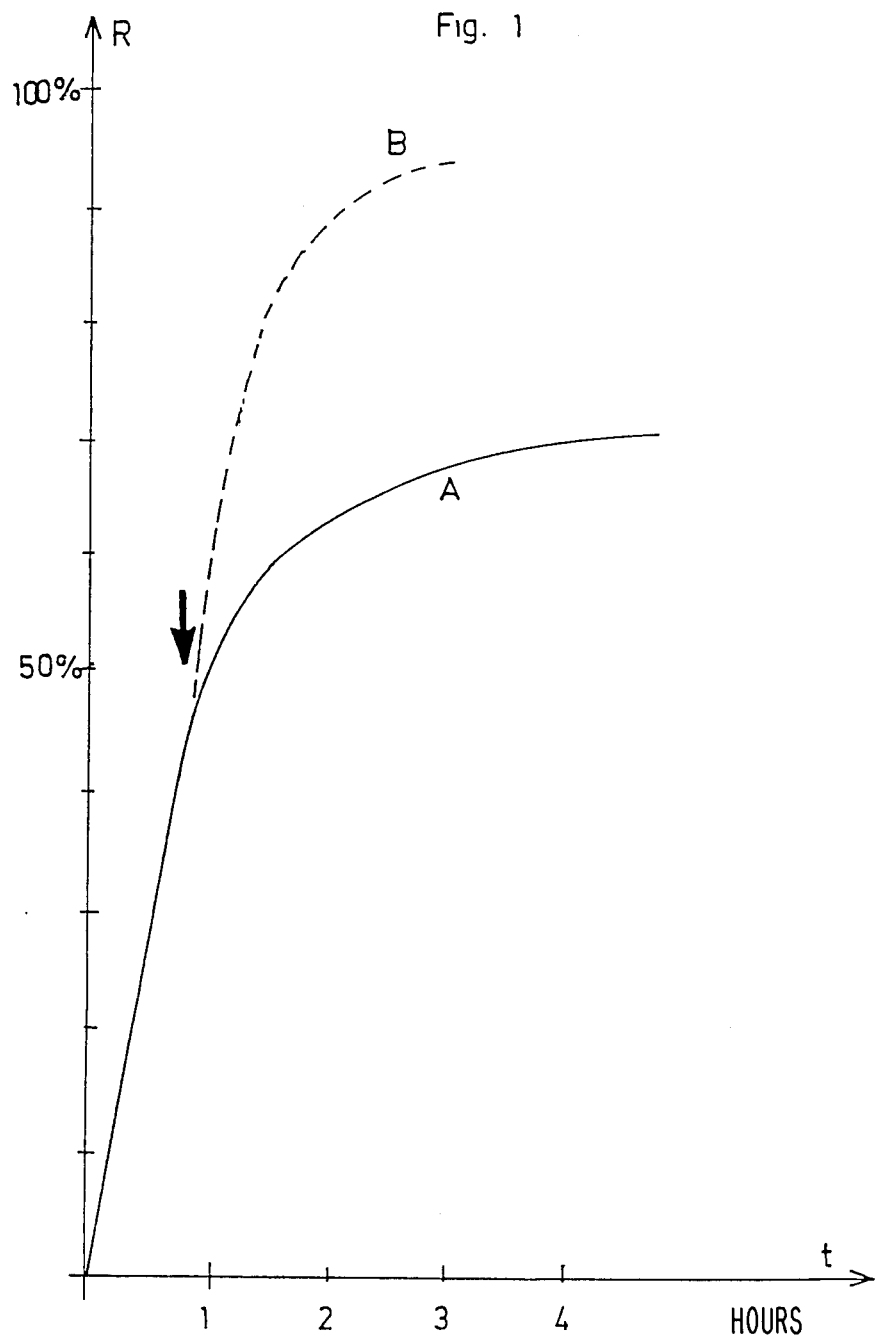

FORMYLATION PROCESS FOR PRODUCING ALDEHYDES

The invention relates to a process for preparing aromatic or heteroaromatic aldehydes by formylation of compounds comprising one or more aromatic or heteroaromatic rings. This invention relates to starting compounds in which the aromatic ring is functionalized by at least one hydroxyl function (in particular phenol compounds) or in which the heteroaromatic ring is nitrogenous (in particular pyrrole compounds).

The Reimer-Tiemann formylation reaction has been known since 1876 and provides for production of phenolic aldehydes from phenols. Interest in this reaction is considerable because the aldehydes so obtained (parahydroxybenzaldehyde or salicylaldehyde) are industrial synthesis intermediates employed in many fields (fine chemistry, pharmacology . . . ); in particular, salicylaldehyde is the forerunner of aspirin.

This reaction comprises placing the initial phenolic compound and chloroform in the presence of an aqueous alkaline hydroxide solution. Since its discovery, this reaction has been modified several times, but its performance has not been significantly improved thereby. Thus, the yield of this reaction is, in the absence of the specific catalyst, about 30% by weight of formed aldehyde with respect to the initial phenol; the best present-day yields are about 50% and have been achieved in the presence of very costly specific catalysts such as ammonium salts or cyclodextrins; (it should be noted that some authors indicate the yield by referring the formed aldehyde to the phenol consumed rather than to the initial phenol, thereby arriving at a higher but spurious value disregarding the substantial residual amounts of phenol). The drawback of low yields achieved to date in the Reimer-Tiemann reaction is accentuated by the fact that the residual phenol is difficult to extract and to recycle, and represents a very serious pollution factor of the aqueous effluents. Moreover, a major drawback of this reaction when applied industrially is its production of substantial amounts of tars which complicates aldehyde extraction. Reference is made to the literature below showing the development of this reaction from its origin to the present:

(1) K. Reimer and F. Tiemann, Berichte 1876, vol. 9, pp 824, 1268, 1285, with data on the reaction fundamentals, (2) U.S. Pat. No. 3,365,500 (1964; Donald F. Pontz), suggesting the addition of methanol or ethanol for improving the yield and directing the reaction toward the para-/form, (3) British patent No. 1,490,350 (1974; ICI), suggesting the use of a phase-transfer catalyst (quaternary ammonium salt), (4) Article of, Y. Sassoon & M. Yonovitch, Tetrahedron Letters, 1979, vol. 39, p 3753, questioning the effects of some phase transfer catalysts, (5) U.S. Pat. No. 4,324,922 (1980; William E. Smith), disclosing pressurization at high temperature, (6) European patent application No. 0 074 272 of 1982; (Sumitomo Chemical Co., Ltd), suggesting the use of a phase transfer catalyst combined with an inert solvent, (7) "The Reimer-Tiemann reaction", Organic Reactions 1982, vol. 28, pp 1-33, survey of this reaction in 1982, (8) Article of, Smith et al, Journal of Organic Chemistry, 1985, V. 50, p 790, stating the extreme difficulty in formylating pyrrole and its derivatives.

These publications together describe a reaction in an aqueous two-phase liquid-liquid medium; the alkaline hydroxide always is added as a more or less concentrated aqueous solution.

Furthermore, the following literature covers the growth of the reaction in an anhydrous solid/liquid medium:

(9) U.S. Pat. No. 3,972,945 (C. F. Albright)

(10) European patent No. 0 068 725 (Sumitomo Chemical Co.)

The authors add alkaline hydroxide in solid form and seek the rigorously anhydrous nature of the medium as the mandatory operative condition. To achieve acceptable reaction performance, they add specific catalysts such as N—N dimethylformamide in the case of patent (9) or a surfactant ("Tween 80", "Span 85") for patent (10). However these procedures incur three serious drawbacks: on one hand pollution of the product obtained by the catalyst, and on the other hand a comparatively low yield, and lastly a residue of the initial compounds in the final products.

Indeed, the progress made since 1876 relative to the Reimer-Tiemann reaction has been of little significance, so that the authors of publication (7) state on page 14:

"Even 105 years after its discovery, conditions for the Reimer-Tiemann reaction cannot be said to have been optimized. This is not too surprising for a reaction in which a quantitative yield has never been reported, and in which useful yields (of abnormal products) of 3–10% are not unusual."

The object of the present invention is to provide a new implementation of the Reimer-Tiemann formylation reaction which makes it simultaneously possible: to increase by considerable and surprising proportions the reaction yield defined as being the number of moles of formed aldehyde with respect to the number of moles of initially used compounds (hereafter, the yields indicated shall be defined by this ratio), to reduce, even totally eliminate, tar formation.

Another object is to make it possible to totally or at least mostly exhaust the aromatic or hetero-aromatic starting compounds.

Another object of the invention is to permit in the case of the phenols, directing the formylation toward the para-/form of the obtained phenol aldehyde.

To that end, the process according to the invention for preparing aromatic or hetero-aromatic aldehydes by formylating aromatic or hetero-aromatic cycles of the initial compounds is of the type wherein the initial reaction compounds comprise at least one aromatic cycle functionalized by at least one hydroxyl function and/or at least one nitrogeneous hetero-aromatic cycle, and comprises placing these initial compounds in the presence of chloroform and excess alkaline hydroxide and, where the alkaline hydroxide is in solid form, in order to carry out a Reimer-Tiemann reaction in a solid/liquid medium; according to the present invention, the initial hydration rate of the medium is adjusted so as to be in a range such that:

the hydration rate is less that 1.5 mole of water per mole of alkaline hydroxide initially present in the medium so as to keep the hydroxide in solid form in the medium, the hydration rate is greater than 0.05 moles of water per mole of starting compound in order that a sufficient quantity of water shall be available at the solid/liquid interface to assure solvation of the reactive species present.

(The expression "excess" relates to the quantity of starting compounds initially used).

Experiments have shown that such a reaction carried out in a heterogeneous and weakly hydrated liquid/solid medium offers absolutely remarkable yields greater than 70% and under certain optimal conditions specified further below up to 95%, also total exhaustion of the initial compounds being accomplished. This result may be explained by the phenomena described below which result from carrying out the reaction in a weakly hydrated, heterogeneous solid/liquid medium. The alkaline hydroxide is in the solid state in the medium and is superficially solvated by the water molecules, weakening the ion bond between the alkaline cation and the hydroxide ion. The latter may thereby react with the chloroform to form dichloro-carbene, which is a highly reactive intermediate body which reacts with the initial compounds to result in the corresponding aldehydes following hydrolysis of the intermediary native forms. It appears that the observed yield and selectivity are due to the role of the water acting as phase transfer element and to the reaction being localized to the solid/liquid interface: the solvation generated by the water at this interface results in the intermediate native substances which in turn lead to the sought-after aromatic or hetero-aromatic aldehydes.

Observations have shown that for less than 0.05 moles of water per mole of initial compounds, the quantity of water will be insufficient to properly solvate the alkaline cations and to release hydroxides in sufficient proportion relative to the initial compounds to initiate the reaction. Above 1.5 moles of water per mole of alkaline hydroxide, the heterogeneous solid/liquid nature of the medium is in jeopardy of being masked by excessive dissolution of the alkaline hydroxide, since the reaction is water producing.

In practice, the best results are obtained by initially adjusting the hydration rate of the reaction medium to between 1 and 2 moles of water per moles of initial compounds (this range is well below the solubility threshold of the alkaline hydroxide, considering that latter is present in excess).

Preferably the alkaline hydroxide is introduced in the reaction medium in solid form as powder or granules in order to increase the solid/liquid contact surface.

In a preferred embodiment which makes it possible to raise the yield to values close to 95% and to exhaust most or all of the initial compounds, alkaline hydroxide in solid form is initially placed in excess into the reaction medium, and alkaline hydroxide in solid form is then added to the reaction medium during the reaction until the initial compounds are exhausted.

Investigation into the reaction kinetics has shown that after a given time of reaction, the yield arrives at a certain level which is interpreted by progressive inactivation of the liquid/solid interface due to anion formation in the medium (chlorides etc.). When alkaline hydroxide is added, preferably at the inflection point of the kinetic curve, it provides a new active solid/liquid interface allowing the reaction to proceed at a satisfactory rate. This addition can be repeated at each curve inflection until the initial compounds are exhausted.

Preferably the initial concentrations are adjusted as follows: the solid alkaline hydroxide is present in excess at a molar ratio greater than 3 with respect to the initial compounds, and in particular at a molar ratio of about 4, the chloroform is present in excess in a molar ratio greater than 3 with respect to the initial compounds, and in particular at a molar ratio of about 10.

It is further known that the Reimer-Tiemann reaction is exothermal but requires energy to feed into the reaction medium. In the process of the invention, it may be desirable on occasion to cool the reaction medium to a temperature between $-10°$ and $+10°$ C. when the reagents are being mixed, and then to heat it through an energy input. This energy input may be carried out: either conventionally, by heating, to raise the medium temperature to $40°$-$60°$ C. or by combining a slight thermal input with ultrasonics, whereby lower-temperature operation is possible between $20°$ and $40°$ C.

The initial compounds may comprise in conventional manner phenol compounds (phenol, guaiacol, syringol, naphtol ... ) or pyrrole compounds (pyrrole, indole ... ).

In the case of a phenol, the addition, known per se, of an alcohol to the reaction medium allows preparing an aldehyde wherein the aldehyde radical is predominantly in the para position to the phenol function.

The alkaline hydroxide used in particular is sodium hydroxide or potassium hydroxide; it has been observed that, just as in the conventional reaction, the use of potassium hydroxide preferentially directs toward the para form of the aldehyde.

Experiment has shown that the addition, known per se, of an inert aprotic solvent (dioxane, toluene ... ) sometimes slightly increases the yield.

The process of the invention is illustrated by the Examples 1 through 9 below. The yield curve of Example 1 is shown in the attached drawing.

EXAMPLE 1

100 cm$^3$ of chloroform, 9.4 g of phenol, 20 g of anhydrous sodium hydroxide and 3.6 cm$^3$ of water are placed in a 250 cm$^3$ reactor provided with a coolant, a mechanical stirrer and a thermometer, and the reaction medium temperature is thermostatically maintained at $50°$ C. These conditions of the initial mixture correspond to a hydration rate of 0.4 moles of water per mole of sodium hydroxide (2 moles of water per mole of initial compound) and to 12.6 times as much chloroform as initial compound (expressed in moles). Thereupon the temperature of the reaction medium is raised to $58°$ C. for one hour. Next 12 g of sodium hydroxide in powdered form are progressively added over a period of two hours, the temperature being kept constant at $58°$ C. The reaction proceeds for 1 hour. At the end of the reaction, the initial phenol has completely disappeared. The residual chloroform is recovered and recycled.

Curve A in FIG. 1 shows the reaction yield R as a function of time (in hours) when there is a single addition of sodium hydroxide at $t=0$. Curve B shows the yield for this Example when, besides the initial addition, a new quantity of sodium hydroxide is added at $t=1$ hour: the reaction kinetics becomes similar again to the original one until a yield of about 85% is achieved ($t=1\frac{1}{2}$ hours); obviously powder sodium hydroxide again may be added to achieve quickly a yield very close to 100%.

The mixture of aldehydes is obtained in sodium form. It is neutralized until a neutral brine is obtained.

The salicylaldehyde can be recovered in conventional manner at a yield close to 77% (9.4 g) with respect to the initial phenol by carrier vapor distillation or by ether extraction.

The p-hydroxybenzaldehyde is recovered at a yield of 17% (2 g) by ether extraction from the acidified residual brine to pH of 1.

The aqueous effluent can be neutralized and does not contain residual toxic phenol products.

EXAMPLE 2

10 cm$^3$ of methanol, 90 cm$^3$ of chloroform and 9.4 g of phenol are placed in a 250 cm$^3$ reactor having a coolant, a mechanical stirrer and a thermometer.

Next 20 g of anhydrous sodium hydroxide powder and 3.6 cm$^3$ of water are added while the previously cooled reaction mixture is kept at 0° C.

These initial mixture conditions correspond to a hydration rate of 0.4 moles of water per mole of sodium hydroxide (2 moles of water per mole of initial compound) and to 11.3 times as much chloroform as the initial compound (expressed in moles).

Thereupon the mixture is slowly returned to ambient temperature and very progressively raised to 58° C.

After 1 hour of reaction, 12 g of powdered sodium hydroxide is progressively added over 2 hours. The temperature is kept constant at 58° C. The reaction is continued for 1 hour.

At the end of the reaction, the initial phenol has entirely vanished. However the residual chloroform lacks purity. It contains secondary products (triphenoxymethanes identified by nuclear magnetic resonance and by infrared spectroscopy).

The phenol aldehyde mixture is in a form combined with sodium. It is neutralized and acidified to a pH of 5. Thereupon the salicylaldehyde is recovered by the conventional carrier vapor distillation of the aqueous phases (following methanol recovery). A yield of 32% (3.9 g) of salicylaldehyde and of 27% (3.2 g) in p-hydroxybenzaldehyde relative to the initial phenol are obtained.

EXAMPLE 3

5 cm$^3$ of dioxane, 95 cm$^3$ of chloroform and 9.4 g of phenol are placed in a 250 cm$^3$ reactor with a coolant, a mechanical stirrer and a thermometer.

Next 15 g of powdered sodium hydroxide and 3 cm$^3$ of water are added while keeping the temperature of the previously cooled reaction mixture at 0° C. These initial mixture conditions correspond to a hydration rate of 0.42 moles of water per mole of sodium hydroxide (2 moles of water per mole of initial compound) and to 11.9 times as much chloroform as the initial compound (expressed in moles).

Thereupon the mixture is slowly returned to ambient temperature and very progressively raised to 58° C. After 1 hour of reaction time, 12 g of powder sodium hydroxide are progressively added over 2 hours. The temperature is kept constant at 58° C. The reaction continues for 1 hour.

At the end of the reaction, the initial phenol has completely vanished. But the residual chloroform lacks purity. As in the previous Example, it contains triphenoxymethanes.

The aldehyde mixture is in sodium form. It is neutralized and acidified to a pH of 5. Thereupon the salicylaldehyde is recovered by conventional aqueous phase carrier vapor distillation. The yield of salicylaldehyde is 46.5% (5.6 g) and that of p-hydroxybenzaldehyde is 37% (4.5 g).

EXAMPLE 4

100 cm$^3$ of chloroform and 9.4 g of phenol are placed in a 250 cm$^3$ reactor with a coolant, a mechanical stirrer and a thermometer.

Thereupon 16.8 g of commercial potassium hydroxide (containing 15% water) and 1.7 g of water are added while the temperature of the reaction mixture, which had been previously cooled, is kept at 0° C.

These initial mixture conditions correspond to a hydration rate of 0.31 moles of water per mole of commercial potassium hydroxide (0.94 moles of water per mole of initial compound) and to 12.6 times as much chloroform as initial compound (expressed in moles).

Thereupon the mixture is slowly returned to ambient temperature and is very gradually raised to 56° C.

After a reaction of 1 hour, 28 g of powdered potassium hydroxide are added over a period of 2 hours. The temperature is kept constant at 58° C. The reaction proceeds for 1 hour.

At the end of the reaction, the initial phenol has completely vanished. But the residual chloroform lacks purity and contains triphenoxymethanes. The salicylaldehyde and the p-hydroxybenzaldehyde are recovered by the above cited techniques. The yield for salicylaldehyde is 38% (4.6 g) and for p-hydroxybenzaldehyde is 17% (2 g).

EXAMPLE 5

100 cm$^3$ of chloroform, 2 g of sodium hydroxide, 1.8 g of $\beta$-naphthol and 0.3 cm$^3$ of water are placed in a 250 cm$^3$ reactor with coolant, mechanical stirrer and thermometer, and the reaction medium temperature is thermostatically kept at 50° C. These initial mixture conditions correspond to a hydration rate of 0.33 moles of water per mole of sodium hydroxide (1.33 moles of water per mole of initial compound) and to 100.8 as much chloroform as initial compound (expressed in moles).

Thereupon the temperature of the reaction medium is raised to 60° C. for 1 hour. Next 1 g of sodium hydroxide powder is added. The reaction proceeds for 3 hours. Following neutralization, the chloroform phase is separated. The aqueous brine is extracted with ether. The organic phases are collected, and 2-hydroxy-1-naphthaldehyde is obtained at a yield of 30%.

EXAMPLE 6

50 cm$^3$ of methanol, 50 cm$^3$ of chloroform and 0.8 g of pyrrole are placed in a 250 cm$^3$ reactor with a coolant, a mechanical stirrer and a thermometer. Then 7 g of commercial potassium hydroxide and 0.5 g of water are added. These initial mixture conditions correspond to a hydration rate of 0.216 moles of water per mole of sodium hydroxide (2.25 moles of water per mole of initial compound (pyrrole) and to 52.5 times as much chloroform as initial compound.

The reaction is subjected to ultrasonics in the "BRANSONIC" tank for 15 hours.

At the end of this reaction, the reaction mixture receives additional water. The chloroform phase then is separated and evaporated-dehydrated on anhydrous sodium sulfate. The yield so obtained in pyrrole carboxaldehydes contained in the chloroform is 15%, a significant amount of chloropyridine being present.

EXAMPLE 7

10 cm$^3$ of methanol and 90 cm$^3$ of chloroform, also 6.2 g of guaiacol are placed in a 250 cm$^3$ reactor with a coolant, a mechanical stirrer and a thermometer. Next 16 g of pulverulent sodium hydroxide and 6 g of water are added while maintaining the mixture temperature at 0° C. These initial mixture conditions correspond to a hydration rate of 0.825 moles of water per mole of sodium hydroxide (6.6 moles of water per mole of initial compound [guaiacol]) and to 22.7 times as much chloroform as initial compound. Thereupon the mixture is slowly returned to ambient temperature and is very gradually raised to 58° C.

Following the reaction, 16 g of pulverulent sodium hydroxide are progressively added over a period of 2 hours. The temperature is kept constant for 1 hour. Then the reaction mixture is cooled to 40° C. and the pH is returned to 2 by gradually adding sulfuric acid. The chloroform phase is then separated from the aqueous phase and is dried on sodium sulfate. The aqueous phase is extracted again with ether. The organic phases next are evaporated. They contain the aldehydes and the residual guaiacol.

The yield is 32% in vanillin (2.4 g) and 38% in isovanillin (2.8 g).

EXAMPLE 8

10 cm$^3$ of methanol, 190 cm$^3$ of chloroform and 7.7 g of syringol are placed in a 250 cm$^3$ reactor having a coolant, a mechanical stirrer and a thermometer. The mixture is treated ultrasonically for 6 hours in a "BRANSONIC" cleaning tank (47 kHz, 180 w, 3 ceramics). After this pretreatment, 8 g of powder sodium hydroxide and 0.9 g of water are added.

These initial mixture conditions correspond to a limit hydration rate of 0.25 moles of water per mole of sodium hydroxide (0.05 moles of water per mole of initial compound) and to 25.2 times as much chloroform as initial compound expressed in moles. For a lesser hydration, the yield drops considerably.

The reaction proceeds in the tank under ultrasonics, at 30° C. and for 2 hours 30 minutes.

As proven by the presence of 2-4 dinitrophenylhydrazine [m.p. 213° C.], the syringaldehyde is obtained with a yield of 12% (1.1 g).

EXAMPLE 9

100 cm$^3$ of chloroform, 9.4 g of phenol, 20 g of powdered sodium hydroxide and 13.5 g of water are placed in a 250 cm$^3$ reactor having a coolant, a mechanical stirrer and a thermometer, keeping the reaction medium temperature at 50° C. by means of a thermostat system. These initial mixture conditions correspond to an upper limit hydration rate of 1.5 moles of water per mole of sodium hydroxide (15 moles of water per mole of substrate) and to 12.6 times as much chloroform as initial compound expressed in moles.

Next the temperature of the reaction medium is raised to 58° C. for 1 hour. Thereupon 12 g of sodium hydroxide powder are progressively added while the temperature is kept constant at 58° C. The reaction proceeds for 1 hour.

At the end of the reaction, some of the initial phenol is still present.

The aldehyde mixture is in sodium form. It is then neutralized until a neutral brine is obtained. The salicylaldehyde may be conventionally recovered at a yield close to 30% (3.6 g) relative to the initial phenol by carrier vapor distillation or by ether extraction. The p-hydroxybenzaldehyde is recovered at a yield of 10.7% (1.3 g) by ether extraction from the acidified residual brine (pH=1).

We claim:

1. A process for the preparation of aromatic or heteroaromatic aldehydes by formylating aromatic or hetero-aromatic rings of starting compounds, wherein the starting compounds comprise at least one aromatic ring having at least one hydroxyl function or at least one nitrogenous hetero-aromatic ring, the process comprising placing the starting compound in the presence of chloroform and an excess of alkaline hydroxide in solid form for bringing about a Reimer-Tiemann reaction in a solid-liquid medium, adding water to the reaction medium so as to adjust the initial hydration rate of the reaction medium so that the hydration rate is less than 1.5 moles of water per mole of initial alkaline hydroxide so as to keep the alkaline hydroxide in solid form and greater than 0.05 moles of water per mole of starting compound so as to maintain sufficient water at the solid/liquid interface for assuring solvation of the reactive species, and carrying out said formylation reaction in the absence of a catalyst.

2. A preparation process as in claim 1, wherein the alkaline hydroxide is introduced into the reaction medium in solid powder or granular form.

3. A preparation process as in claim 1 wherein solid alkaline hydroxide is initially introduced in excess into the reaction medium, characterized in that subsequently solid alkaline hydroxide is added to the reaction medium during the reaction until the initial compounds are exhausted.

4. A preparation process as in claim 1 wherein initially: the solid alkaline hydroxide is present in excess by a molar ratio greater than 3 with respect to the initial compounds, the chloroform is present in excess by a molar ratio greater than 3 with respect to the initial compounds.

5. A preparation process as in claim 1 and wherein the alkaline hydroxide is initially placed in dehydrated or slightly hydrated form into a reactor together with a liquid mixture of chloroform and initial compounds and in that water is added in sufficient amount to adjust the hydration rate of the medium within the above cited range.

6. A preparation process as in claim 1 wherein the reaction medium is cooled while the reagents are mixed to a temperature between −10° and +10° C. and then is progressively heated until its temperature is raised to between 40° and 65° C.

7. A preparation process as in claim 1 and wherein the reaction medium is cooled during the mixing of the reagents to a temperature between −10° and +10° C. and then is kept at a value between 20° and 40° C. and subjected to ultrasonic energy.

8. A preparation process as in claim 1 and wherein initially the hydration rate of the reaction medium is adjusted between 1 and 2 moles of water per mole of initial compounds.

9. A preparation process as in claim 1 wherein the initial compounds are phenol compounds or pyrrole compounds.

10. A preparation process as in claim 1 for preparing an aldehyde from a phenol, wherein the aldehyde radical is mostly in the para position of the phenol function, and comprising adding an alcohol to the reaction medium.

11. A preparation process as in one of claim 1 wherein an inert aprotic solvent is added to the reaction medium.

12. A preparation process as in claim 1 wherein the alkaline hydroxide is sodium hydroxide or potassium hydroxide.

* * * * *